(12) United States Patent
Kodali et al.

(10) Patent No.: US 10,113,051 B2
(45) Date of Patent: Oct. 30, 2018

(54) EPOXY ESTOLIDE FATTY ACID ALKYL ESTERS USEFUL AS BIORENEWABLE PLASTICIZERS

(71) Applicant: Regents of the University of Minnesota, Minneapolis, MN (US)

(72) Inventors: Dharma Kodali, Minneapolis, MN (US); Lucas J. Stolp, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/893,601

(22) PCT Filed: May 30, 2014

(86) PCT No.: PCT/US2014/040306
§ 371 (c)(1),
(2) Date: Nov. 24, 2015

(87) PCT Pub. No.: WO2014/197327
PCT Pub. Date: Dec. 11, 2014

(65) Prior Publication Data
US 2016/0108206 A1    Apr. 21, 2016

Related U.S. Application Data

(60) Provisional application No. 61/830,223, filed on Jun. 3, 2013.

(51) Int. Cl.
*C08K 5/1515* (2006.01)
*C08K 5/00* (2006.01)
(Continued)

(52) U.S. Cl.
CPC .......... *C08K 5/1515* (2013.01); *C07D 303/42* (2013.01); *C08K 5/0016* (2013.01); *C08K 5/101* (2013.01)

(58) Field of Classification Search
CPC .... C08K 5/101; C08K 5/0016; C08K 5/1515; C07D 303/42
See application file for complete search history.

(56) References Cited

U.S. PATENT DOCUMENTS 2,448,602 A    9/1948 Kester et al.
2,624,680 A    1/1953 Swern
(Continued)

FOREIGN PATENT DOCUMENTS

DE              4433958 A1    3/1996
WO    WO2009033240 A1    3/2009
(Continued)

OTHER PUBLICATIONS

Lipid Synthesis and Manufacture, p. 413 (Year: 1999).*
(Continued)

*Primary Examiner* — Melvin C. Mayes
*Assistant Examiner* — Stefanie J Cohen
(74) *Attorney, Agent, or Firm* — Fish & Richardson P.C.

(57) ABSTRACT

A composition is described that includes epoxy estolide fatty acid alkyl esters derived from triacylglycerol oil having an unsaturation of greater than 80 Iodine Value ("IV"). The esters are useful as plasticizers for a variety of polymers. Examples of triacylglycerol oils include vegetable oils such as soybean oil, castor oil, canola oil, rapeseed oil, sunflower oil, corn oil, safflower oil, camelina oil, and linseed oil.

15 Claims, 10 Drawing Sheets

(51) Int. Cl.
*C07D 303/42* (2006.01)
*C08K 5/101* (2006.01)

(56) References Cited

U.S. PATENT DOCUMENTS

| | | |
|---|---|---|
| 4,124,558 A | 11/1978 | Miller |
| 5,075,046 A | 12/1991 | Stoll |
| 6,018,063 A | 1/2000 | Isbell |
| 6,734,241 B1 | 5/2004 | Nielsen |
| 6,797,753 B2 | 9/2004 | Benecke |
| 6,949,597 B2 | 9/2005 | Nielsen |
| 7,196,124 B2 | 3/2007 | Parker |
| 8,258,326 B1 † | 9/2012 | Forest |
| 8,383,708 B2 | 2/2013 | Geng |
| 8,580,985 B2 † | 11/2013 | Thompson |
| 9,315,650 B2 | 4/2016 | Kodali |
| 2006/0020062 A1 | 1/2006 | Bloom |
| 2008/0200595 A1 | 8/2008 | Hinault |
| 2010/0010127 A1 | 1/2010 | Barki |
| 2010/0154292 A1 | 6/2010 | Zhou |
| 2012/0085568 A1 | 4/2012 | Eaton |
| 2012/0289727 A1 | 11/2012 | Cordeiro |
| 2013/0053589 A1 | 2/2013 | Forest |
| 2013/0131302 A1 | 5/2013 | Suppes |
| 2013/0228097 A1 | 9/2013 | Kodali |
| 2013/0324754 A1 | 12/2013 | Bredsguard |
| 2014/0213709 A1 | 7/2014 | Dakka |
| 2016/0009673 A1 | 1/2016 | Kazemizadeh |
| 2017/0096542 A1 | 4/2017 | Kodali et al. |

FOREIGN PATENT DOCUMENTS

| | | |
|---|---|---|
| WO | WO2009138508 A1 | 11/2009 |
| WO | WO2011021107 A2 | 2/2011 |
| WO | WO2011041380 A1 | 4/2011 |
| WO | WO2011046736 A2 | 4/2011 |
| WO | WO2012036913 A2 | 3/2012 |
| WO | WO2012173666 A1 | 12/2012 |
| WO | WO2014197327 A1 | 12/2014 |

OTHER PUBLICATIONS

Isbell, chemistry and physical properties of estolides, grasad and aceites, 62 (1), pp. 8-20 (Year: 2011).*
Greenspan et al, epoxy fatty acid ester plasticizers, industrial and engineering chemistry, vol. 45, No. 12, pp. 2722-2726 (Year: 1953).*
Third-Party Submission under 37 CFR 1.290, filed Apr. 28, 2016, 7 pages.
International Search Report and Written Opinion for PCT/US2014/040306, dated Oct. 15, 2014, 11 pages.
International Preliminary Report on Patentability for PCT/US2014/040306, dated Dec. 17, 2014, 7 pages.
U.S. Appl. No. 15/277,325, filed Sep. 27, 2016.

\* cited by examiner
† cited by third party

EPOXY ESTOLIDE FATTY ACID ALKYL ESTERS USEFUL AS BIORENEWABLE PLASTICIZERS

This application is a National Stage application under 35 U.S.C. § 371 of International Application No. PCT/US2014/040306, having an International Filing Date of May 30, 2014, which claims priority from U.S. Provisional Application Ser. No. 61/830,223, filed Jun. 3, 2013.

TECHNICAL FIELD

This invention relates to biorenewable plasticizers.

BACKGROUND

Plasticizers are non-volatile liquid compounds that impart flexibility to polymers and increase their range of end applications. The majority of plasticizers are used in the utilization of polyvinylchloride (PVC). PVC, due to its unique combination of price, performance, and versatile use, is one of the oldest and widely used high volume plastics. The PVC products formulated with various additives, range from very rigid pipes and siding to flexible flooring, sheeting, and adhesives. The compounding of PVC includes multifunctional additives that modify the properties; in general the formulations contain the polymer (resin), thermal stabilizers, fillers, plasticizers, and other specific property enhancers such as fire resistant materials. Rigid PVC may contain low levels of plasticizer usually less than 20 phr (parts per hundred parts resin) and is primarily used for pipe work, ducts, and similar applications where structural rigidity and chemical resistance is required. Flexible PVC contains high concentrations of plasticizer (up to 100+ phr) and is useful for numerous applications such as films, sheeting, cable coverings, moldings, stationary products, toys, hoses, leather goods, clothing and various furnishings.

The dominant class of plasticizers used in the vinyl industry today is the petroleum-derived phthalates. These compounds are produced by reacting phthalic anhydride with two equivalents of alcohol to form a diester. The largest produced phthalate for the vinyl industry is dioctyl phthalate (DOP).

Materials derived from natural/renewable resources have been proposed as alternatives to phthalate plasticizers. One example is a fully acylated monoglyceride ester derived from hydrogenated castor oil described, e.g., in U.S. Pat. Nos. 6,734,241 and 6,949,597, and sold under the name "Soft-n-Safe" by Danisco. Other examples include epoxidized fatty acid esters derived from epoxidized oils, such as linseed and soybean, trans-esterified with various polyols, as described, e.g., in U.S. Pat. No. 6,797,753.

Another example, described in WO2009/033240, features a mixture of glycerol esters containing natural fatty acyl chains and short acetyl groups, along with fatty acid ethyl esters. It appears that the unsaturated fatty acids are not modified and there are no fatty acyl chain backbone modifications to increase the polarity. In yet another example, described in WO2012/036913, estolide fatty acid esters and their use as plasticizers are described. These esters lack epoxy groups.

SUMMARY

A composition is described that includes epoxy estolide fatty acid alkyl esters derived from triacylglycerol oil having an unsaturation of greater than 80 Iodine Value ("IV").

Examples of triacylglycerol oils include vegetable oils such as soybean oil, castor oil, canola oil, rapeseed oil, sunflower oil, corn oil, safflower oil, camelina oil, and linseed oil.

An "epoxy estolide fatty acid alkyl ester" is a long chain fatty acid alkyl ester having both epoxy and estolide functionalities attached to the backbone carbon atoms of the fatty acid.

The fatty acid alkyl esters can be $C_1$-$C_6$ alkyl esters or $C_1$-$C_{12}$ alkyl esters. Examples include methyl and n-butyl esters. Examples of suitable epoxy estolide esters include esters derived from carboxylic acids having 1 to 4 carbon atoms, e.g., acetate esters.

The compositions are useful as plasticizing agents when combined with a polymer such as polyvinyl chloride, or biopolymers such as polylactides or cellulosics (e.g., cellulose acetate), in an amount sufficient to plasticize the polymer or biopolymer.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
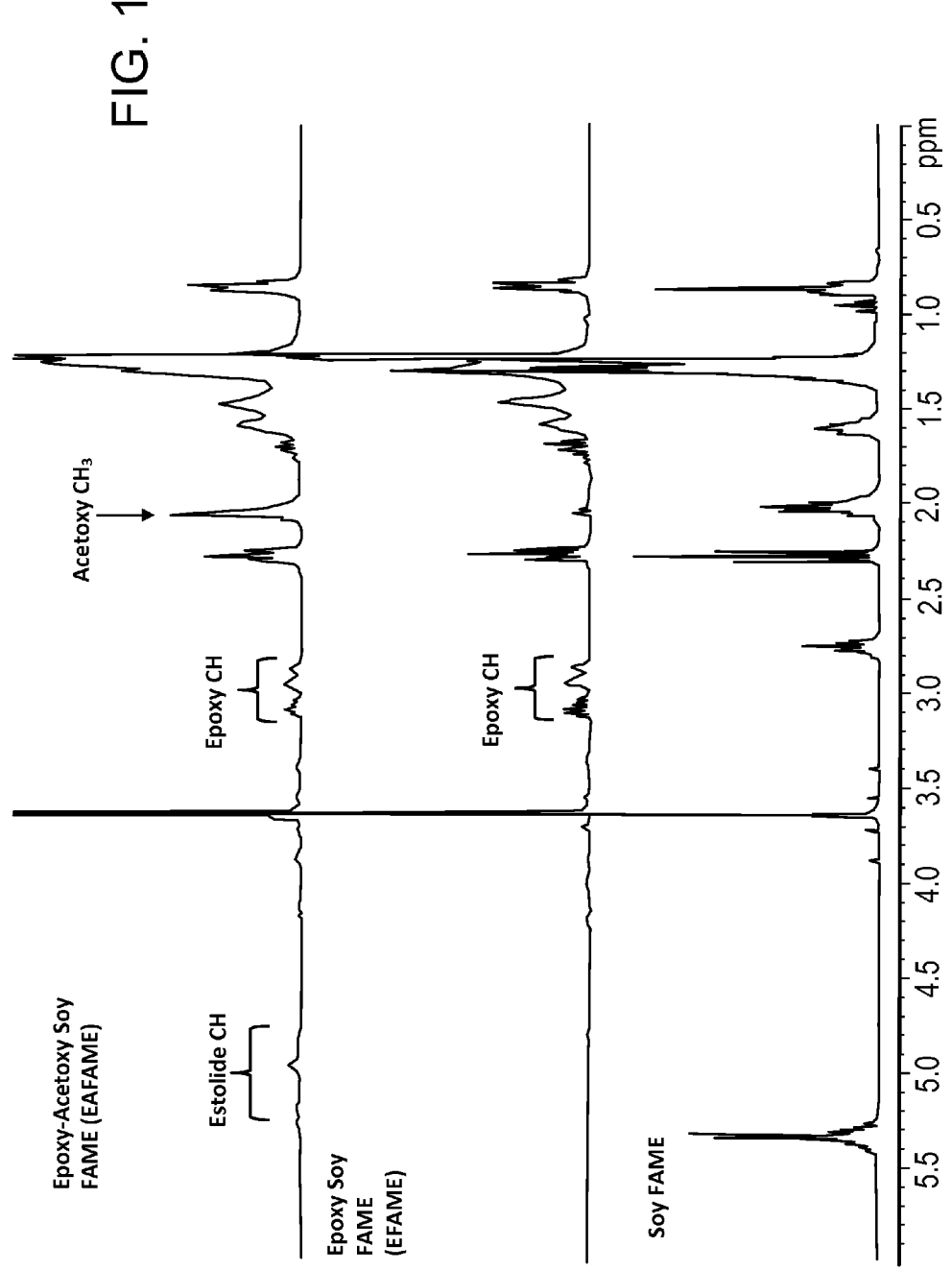
FIG. 1 depicts proton NMR spectra of Soy Fatty Acid Methyl Ester (SoyFAME), Epoxy Soy FAME (EFAME), and Epoxy-Acetoxy Soy FAME (EAFAME) compounds.

Epoxy estolide fatty acid alkyl esters are described in the Summary of the Invention, above. These esters may be derived from a variety of animal and plant sources, including vegetable oils, fish oil, algal oil, oils made by fermentation, and fractionated oils from tallow or lard. The synthesis of such esters will now be described with reference to epoxy acetoxy fatty acid methyl and n-butyl esters. However, the reaction schemes are equally applicable to other estolide fatty acid alkyl esters.

Reaction Scheme 1

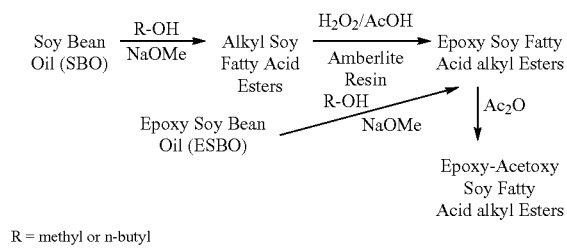

R = methyl or n-butyl

Using a vegetable oil such as soybean oil (SBO) as a starting material, transesterification with methanol or n-butanol (R=CH$_3$ or C$_4$H$_9$) produces the respective alkyl soy fatty acid esters. Alternatively n-butyl esters can be produced from commercially available fatty acid methyl esters (FAME) by transesterification with n-butanol. These esters can then be epoxidized using standard epoxidation methods. For example, as shown in Reaction Scheme 1, the epoxidation may be carried out using hydrogen peroxide, acetic acid, and Amberlite IR 120 H$^+$ ion exchange resin. The epoxidized esters produced are then partially acetylated using acetic anhydride to form the product esters having epoxy-acetoxy functionality. Alternatively, commercially available Epoxidized Soybean Oil (ESBO) may be used, as also shown in Reaction Scheme 1. Using epoxidized oil as the starting material reduces the number of synthetic steps, thus reducing costs.

Reaction Scheme 2

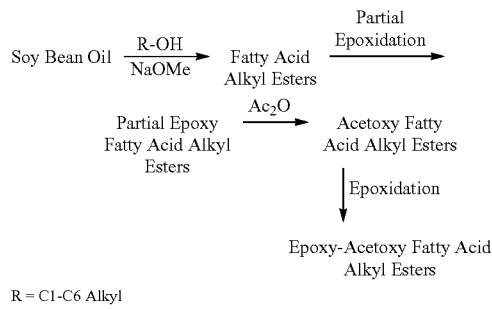

R = C1-C6 Alkyl

The resulting epoxy estolide esters derived from Reaction Scheme 1 contain some cyclic ether moieties that might limit plasticizer functionality. Reaction Scheme 2 provides an alternative route to make the final products having reduced amounts of cyclic ether moieties. In this reaction scheme, the unsaturated fatty acid esters are partially epoxidized and acetylated. After the acetylation of the epoxy groups, the remaining double bonds are epoxidized, resulting in a material containing little or no cyclic ether moieties, but containing the epoxy-acetoxy functionality.

Reaction Scheme 3

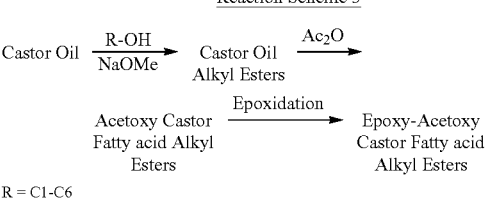

R = C1-C6

In another modification, castor oil fatty acid alkyl esters are used as a starting material to prepare an epoxy estolide product, specifically 9,10-epoxy-12-acetoxyalkylstearate. The synthesis of this material is shown in Reaction Scheme 3. For any of these syntheses, the use of C$_1$-C$_6$ alcohols will provide different head group esters. Similarly, the use of different anhydrides to open the epoxy function creates a variety of branched estolides.

The preparation of specific epoxy estolide fatty acid alkyl esters, and their use as plasticizers, will now be described.

Synthetic Procedures

1. Soy Fatty Acid Methyl Esters (FAME) and Soy Fatty Acid n-Butyl Esters (FAnBE)

Soy Fatty Acid Methyl Esters (FAME) or soy-based biodiesel is available commercially and used without further purification. Fatty Acid n-Butyl Esters can be prepared by the transesterification of Soybean Oil or Soy FAME using excess n-butanol in the presence of a base catalyst according to known procedures.

2. Epoxy Soy Fatty Acid Methyl Esters (EFAME)

A baffled reactor equipped with mechanical stirring and a reflux condenser was charged with 2.5 kg of FAME, 0.5 mol per double bond of acetic acid, 1.1 mol per double bond of 50% H$_2$O$_2$, and 5 wt % of dried Amberlite IR 120 H$^+$ ion exchange resin. The flask was stirred at 1200 RPM and heated to 60° C. The heat was removed and the exothermic reaction was allowed to further heat the reaction mixture to 75° C. The reaction temperature was maintained at 75° C. with external cooling for 1 hour, followed by external heating for an additional 6 hours. The reaction mixture was filtered under vacuum and allowed to separate into two layers. The aqueous layer was removed and the organic layer was vacuum distilled to remove excess acetic acid. After distillation the material was stirred with 2% Magnesol and filtered under vacuum to yield Epoxy Fatty Acid Methyl Ester (EFAME) quantitatively (2.75 kg) as a pale yellow oil (Gardner color number 1).

Using a similar procedure Epoxy Fatty Acid n-Buyl Esters (EFAnBE) can be prepared starting from soy fatty acid n-butyl esters, in quantitative yield as a pale yellow oil (Gardner color number 1).

3. Epoxy-Acetoxy Fatty Acid Methyl Esters (EAFAME)

A flask equipped with a reflux condenser containing 2.0 kg EFAME and acetic anhydride (0.5 mol per original double bond) was heated to 130° C. while magnetically stirring. After reacting for 12 hours, the contents of the flask were cooled to room temperature, where excess acetic anhydride was allowed to react with added H$_2$O (5% w/w EFAME) for 30 minutes. The product was bleached by the addition of H$_2$O$_2$ (4% w/w Epoxy Fatty Acid Esters) (50% w/w H$_2$O) for 1-3 days depending on the level of bleaching desired. The acetic acid and H$_2$O$_2$ were removed by vacuum distillation to yield Epoxy-Acetoxy Fatty Acid Methyl Esters (EASFAME) quantitatively (2.0 kg) as light yellow colored oil (Gardner color number 1).

The EASFAME, EFAME, and SoyFAME materials were characterized by proton NMR. The results are shown in FIG. 1.

4. Epoxy-Acetoxy Fatty Acid n-Butyl Esters (EAFAnBE)

EAFAnBE is prepared employing a similar procedure described above for EAFAME, starting from Epoxy Fatty Acid n-Buyl Esters (EFAnBE), resulting in a quantitative yield of EAFAnBE as a light yellow oil (Gardner color number 1).

5. Castor Oil Fatty Acid Methyl Ester (COFAME)

A flask containing 100 g of Castor Oil was heated to 120° C. under vacuum for 1 hour to remove moisture. The flask was cooled to 60° C., after which 100 mL of anhydrous methanol and 1% NaOMe were added under an inert atmosphere. The contents of the flask were heated to reflux and reacted until the disappearance of the Castor Oil spot on TLC (80/20 isopropyl ether/hexanes) was observed. The excess methanol was removed by distillation, causing the separation of the glycerol and COFAME into two phases. The glycerol phase was removed and the COFAME was diluted with ethyl acetate, washed three times with brine, and dried over sodium sulfate. The solvent was removed in vacuo, resulting in Castor Oil Fatty Acid Methyl Ester (COFAME) as a light yellow oil (Gardner number 2-3).

6. Acetylated Castor Oil Fatty Acid Methyl Esters (ACOFAME)

A flask containing 70 g COFAME and 22.7 mL (1.1 mol per OH) acetic anhydride were heated to 100° C. for 8 hours. The contents were cooled to room temperature, diluted with ethyl acetate, washed three times with water, once with saturated $NaHCO_3$, and once with brine, and then dried over $NaSO_4$. The solvent was removed in vacuo, resulting in a 92% yield of Acetylated Castor Oil Fatty Acid Methyl Esters (ACOFAME) as a yellow oil (Gardner color number 4).

7. Epoxy-Acetoxy Castor Oil Fatty Acid Methyl Esters (EACOFAME)

A flask containing 10 grams of ACOFAME, 0.79 mL (0.5 mol per double bond) of acetic acid, and 0.5 g (5 wt %) of Amberlite IR 120 $H^+$ form ion exchange resin was heated to 75° C. To the flask was added 1.8 mL (1.1 mol per double bond) 50% $H_2O_2$. The flask was maintained at 75° C. with a heated water bath for 5 hours. The reaction mixture was diluted with ethyl acetate, decanted off from the ion exchange resin, washed three times with water, once with saturated $NaHCO_3$, and once with brine, and then dried over $NaSO_4$. The solvent was removed in vacuo, resulting in Epoxy-Acetoxy Castor Oil Fatty Acid Methyl Esters (EACOFAME) in quantitative yield as a pale yellow oil (Gardner color number <1).

Figure 2:
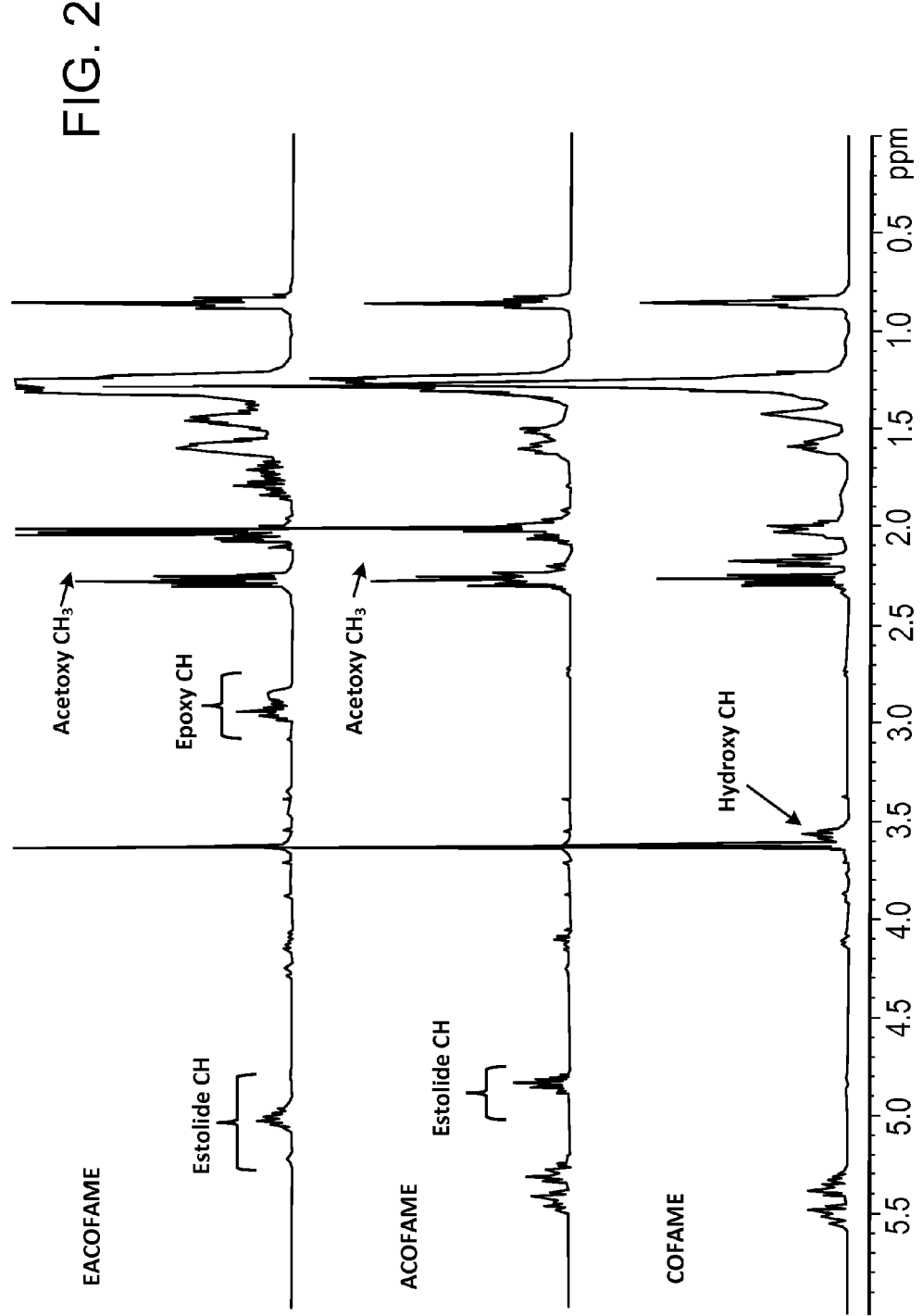
FIG. 2 depicts proton NMR spectra of Castor Oil Fatty Acid Methyl Ester (COFAME), Acetoxy Castor Oil FAME (ACOFAME), and Epoxy-Acetoxy Castor Oil FAME (EACOFAME).

The EACOFAME, ACOFAME, and COFAME materials were characterized by proton NMR. The results are shown in FIG. 2.

8. Epoxy-Acetoxy Castor Oil Fatty Acid n-Butyl Esters (EACOFAnBE)

The n-butyl derivatives of castor oil were prepared by transesterificaton of castor oil with n-butyl alcohol according to the general procedure described in Example 5, followed by acetylation and epoxidation following the procedures of Examples 6 and 7.

Plasticizer Evaluation

A. EAFAME and EAFAnBe

EAFAME and EAFAnBE were evaluated for use as PVC plasticizers. Two commercial plasticizers, diisononyl phthalate (DINP) and 1,2-cyclohexane dicarboxylic acid diisononyl ester (DINCH), were also evaluated for comparison. The physical properties of the plasticizers used are set forth below in Table 1.

TABLE 1

| Plasticizer | Acid Value (mg KOH/g) | Color (Gardner) | Viscosity @ 20° C. (mPa*s) |
|---|---|---|---|
| DINP | 0.01 | <1 | 75 |
| DINCH | 0.07 | <1 | 50 |
| EAFAME | 4.37 | 1 | 52 |
| EAFAnBE | 1.96 | 1 | 90 |
| EACOFAME | <1 | <1 | 64 |

Figure 3:
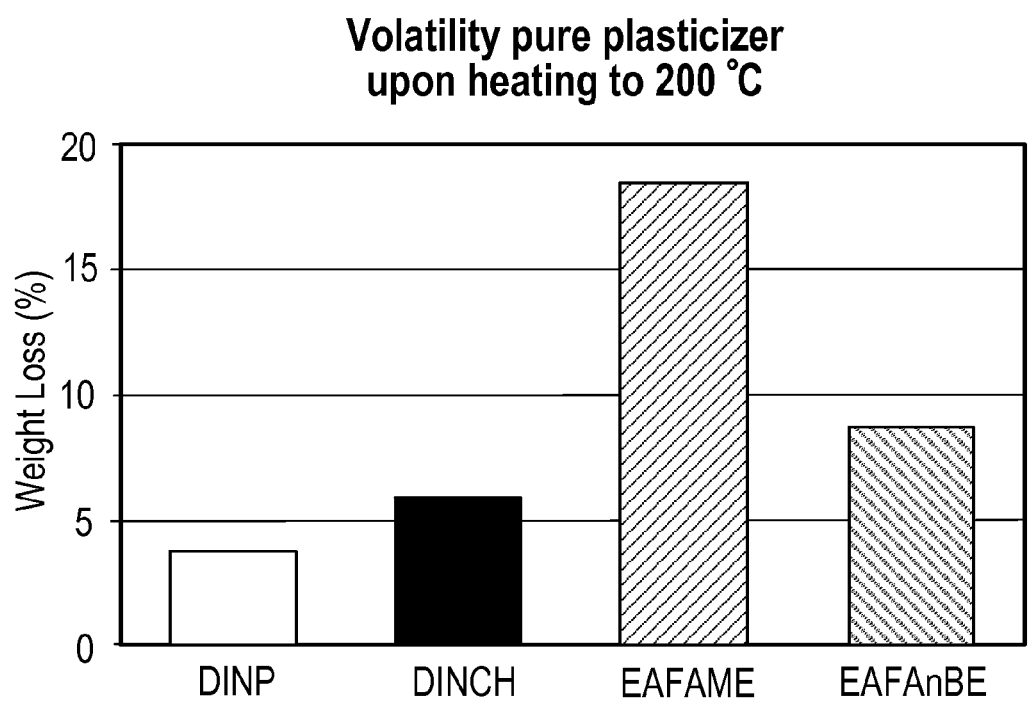
FIG. 3 illustrates the volatility of EAFAME and EAFAnBE plasticizers, compared to commercial DINP and DINCH plasticizers, after 10 minutes at 200° C.

The volatility of each plasticizer was evaluated by heating a quantity to 200° C. and monitoring the weight loss over time. The weight loss of the plasticizers after 10 min at 200° C. is shown in FIG. 3.

The plasticizers were compounded with PVC to make PVC plastisols. 50 phr plasticizer was combined with 100 phr PVC (Vestolit B7021 ultra available from Evonlik Industries), 3 phr of Epoxidized Soy Bean Oil (ESBO, available from Chemtura as Drapex 39), and 2 phr Ca/Zn stabilizer (available from Chemtura as Mark CZ 149) to form a paste. The paste was spread onto a 1 mm thick sheet and heated to 200° C. in a Mathis oven for 2 minutes. The plastisol sheets thus formed were then evaluated for various plasticizer properties.

Figure 4:
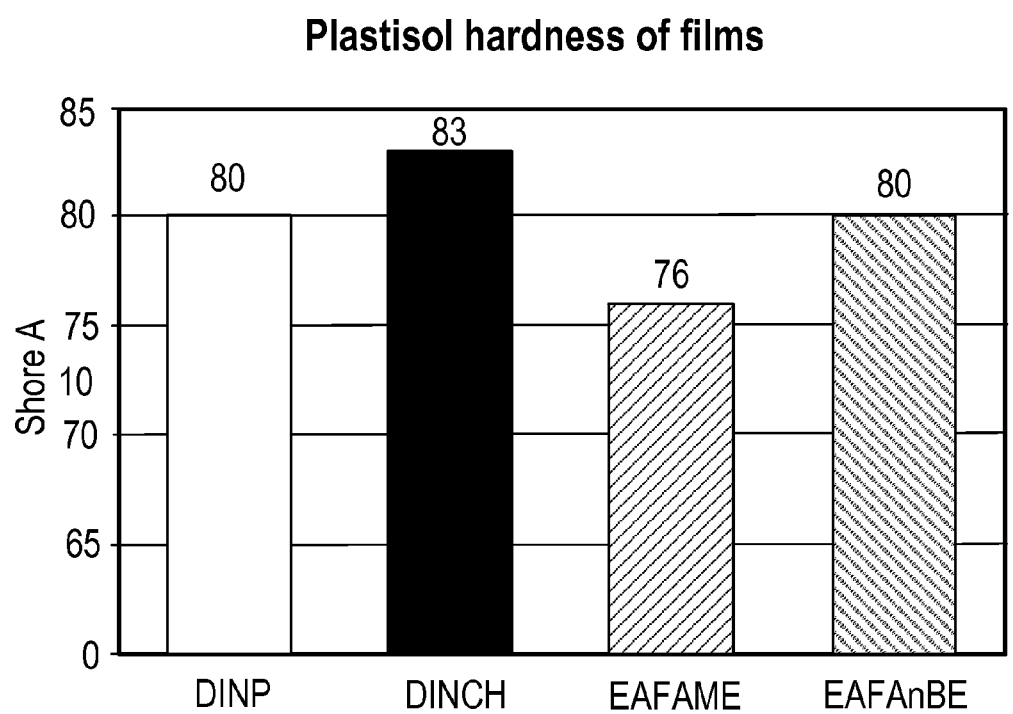
FIG. 4 illustrates the Shore A hardness of plastisols prepared with EAFAME and EAFAnBE plasticizers, compared to commercial DINP and DINCH plasticizers.

The Shore A hardness of each plastisol sheet was measured according to ASTM D2240. The results are shown in FIG. 4. The higher efficiency of the plasticizer is indicated by a lower Shore A hardness. The efficiencies of AEFAME and AEFAnBE plasticizers were comparable to or better than the two commercial plasticizers.

Figure 5:
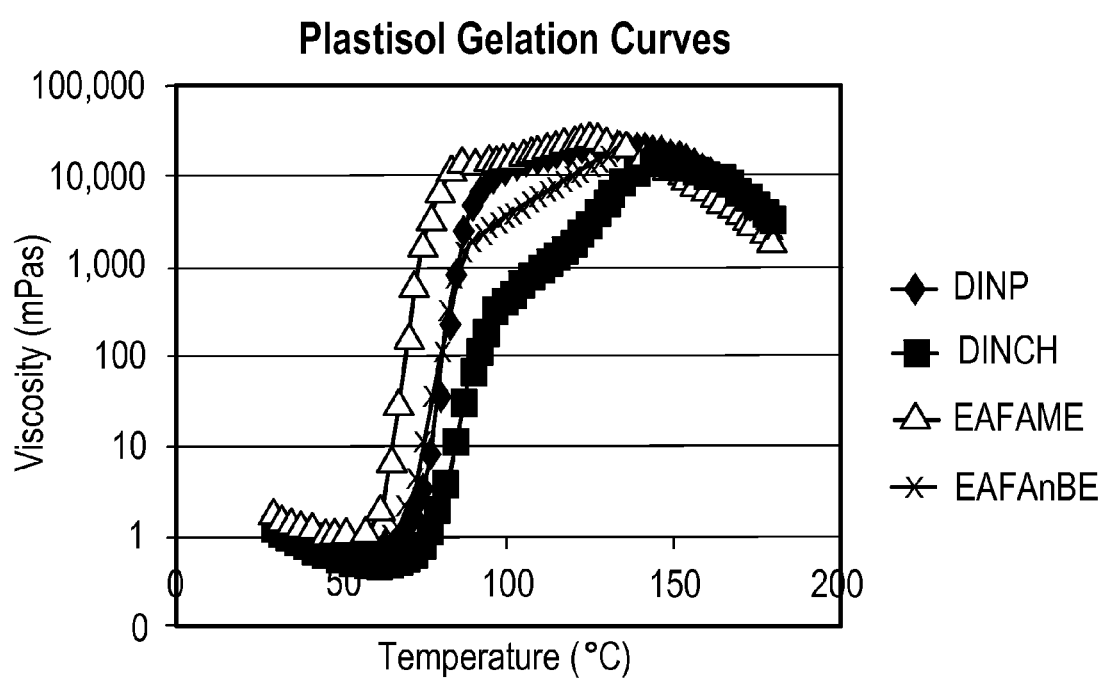
FIG. 5 illustrates the gelation behavior of plastisols prepared with EAFAME and EAFAnBE plasticizers, compared to commercial DINP and DINCH plasticizers.

The gelation behavior of each plastisol was determined by measuring changes in viscosity with temperature. The results are shown in FIG. 5. Both EAFAnBE and EAFAME demonstrated faster gelation than DINCH. The gelation behavior of EAFAnBE was comparable to DINP, while EAFAME was faster, indicating better fusion and processing characteristics.

The thermal stability of each plastisol sheet was evaluated by thermally aging a strip of each sheet in a conveyer oven at 200° C. Strips prepared with DINP and DINCH began to discolor and blacken after 10 minutes, whereas strips prepared with EAFAnBE and EAFAME remained light colored even after 12 minutes, demonstrating greater thermal stability relative to the DINP and DINCH strips.

Figure 6:
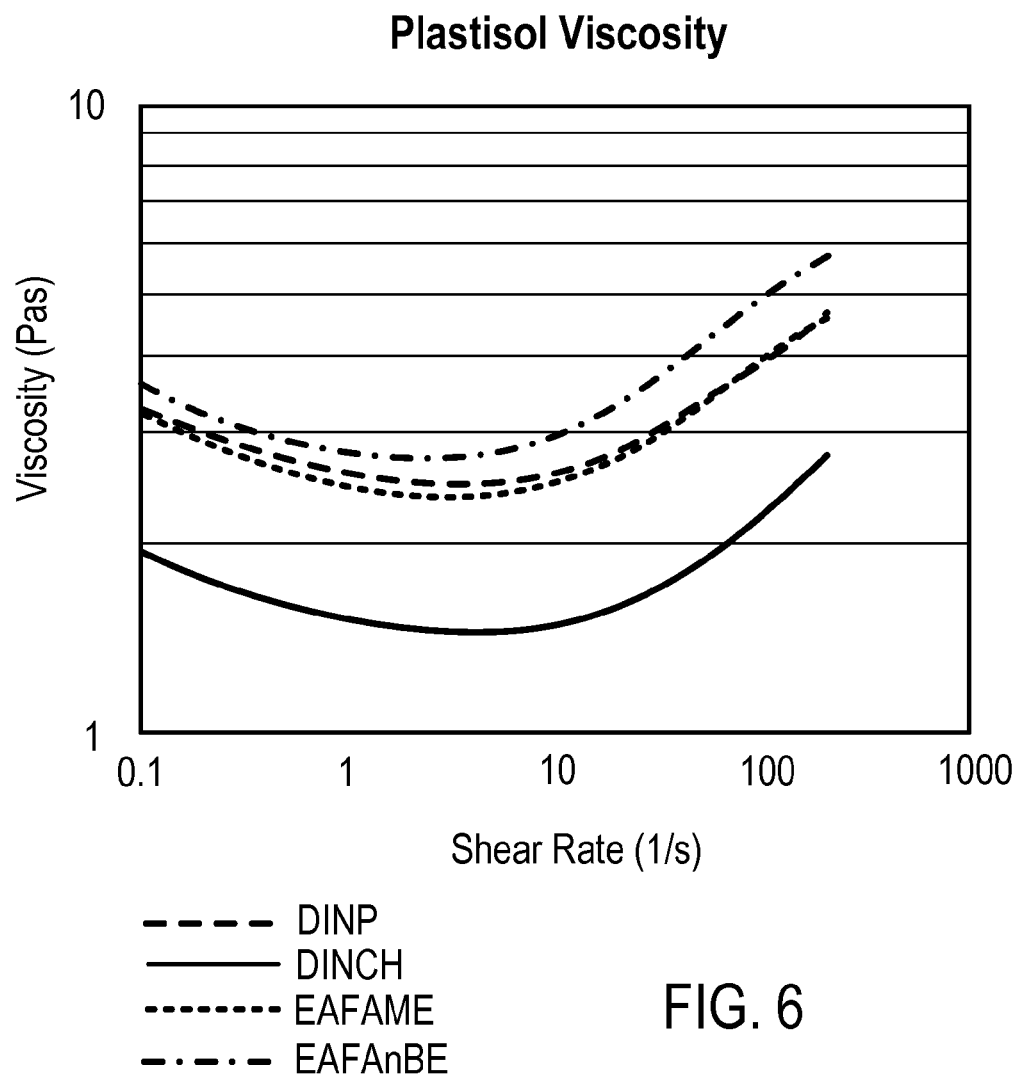
FIG. 6 illustrates viscosity profiles for plastisols prepared with EAFAME and EAFAnBE plasticizers, compared to commercial DINP and DINCH plasticizers.

The change in viscosity with shear of each plastisol was measured. The results are shown in FIG. 6. The results demonstrate that EAFAnBE and EAFAME had viscosities similar to that of DINP, suggesting that their processability would be similar.

Figure 7:
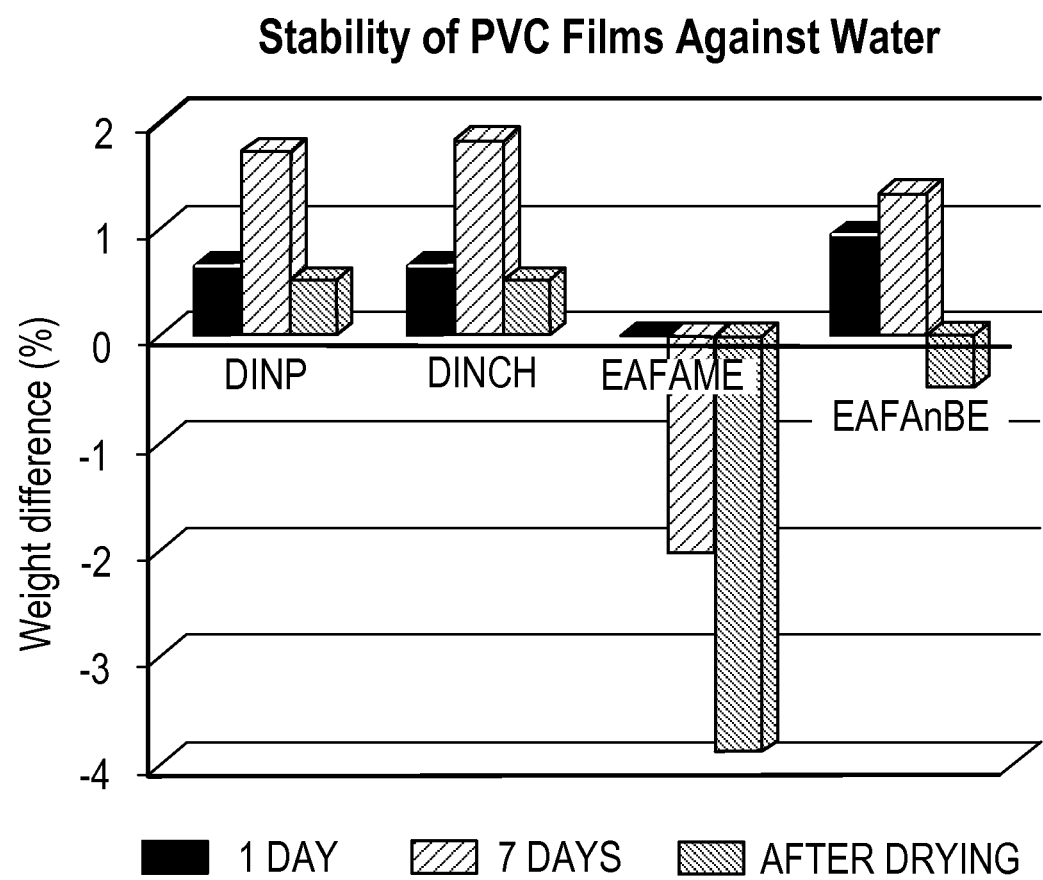
FIG. 7 illustrates the stability in water for plastisols prepared with EAFAME and EAFAnBE plasticizers, compared to commercial DINP and DINCH plasticizers.
Figure 8:
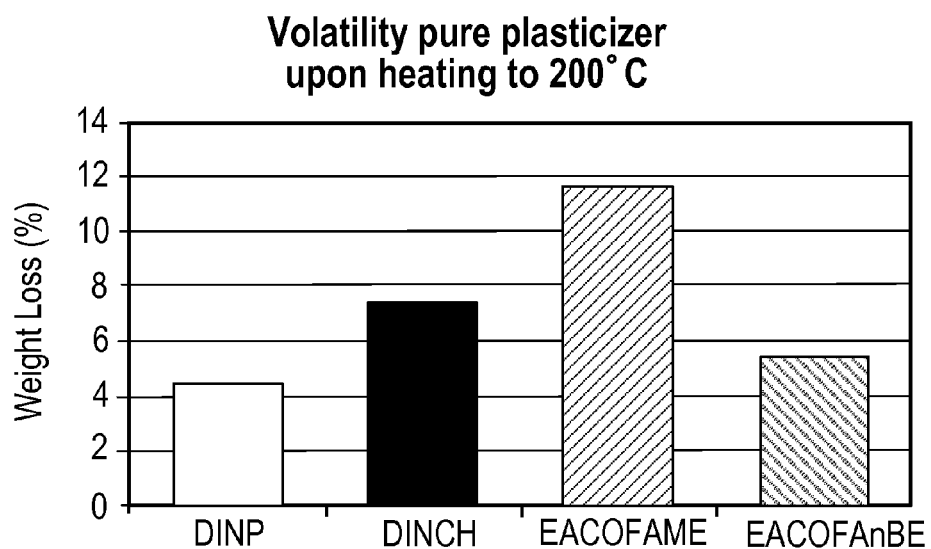
FIG. 8 illustrates the volatility of EACOFAME and EACOFAnBE plasticizers, compared to commercial DINP and DINCH plasticizers, after 10 minutes at 200° C.
Figure 9:
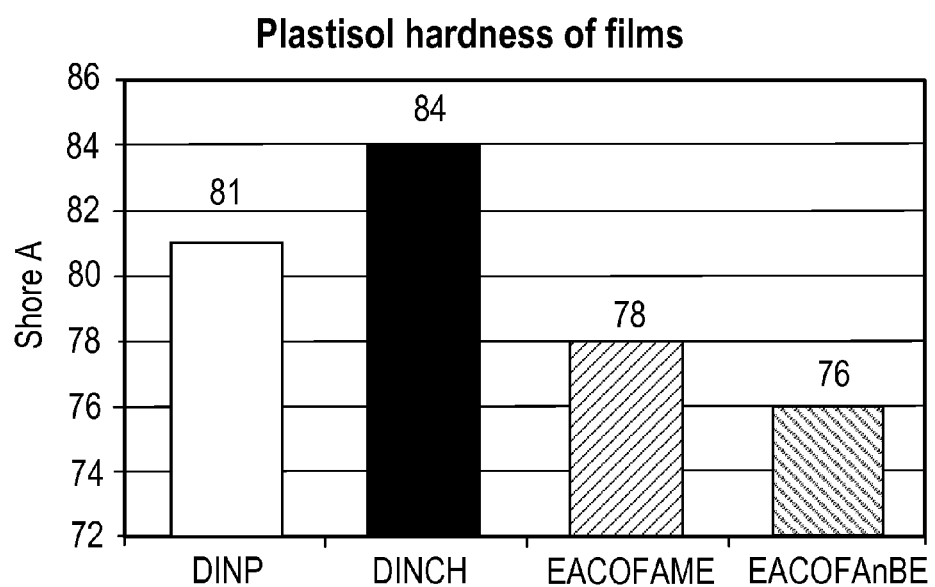
FIG. 9 illustrates the Shore A hardness of plastisols prepared with EACOFAME and EACOFAnBE plasticizers, compared to commercial DINP and DINCH plasticizers.
Figure 10:
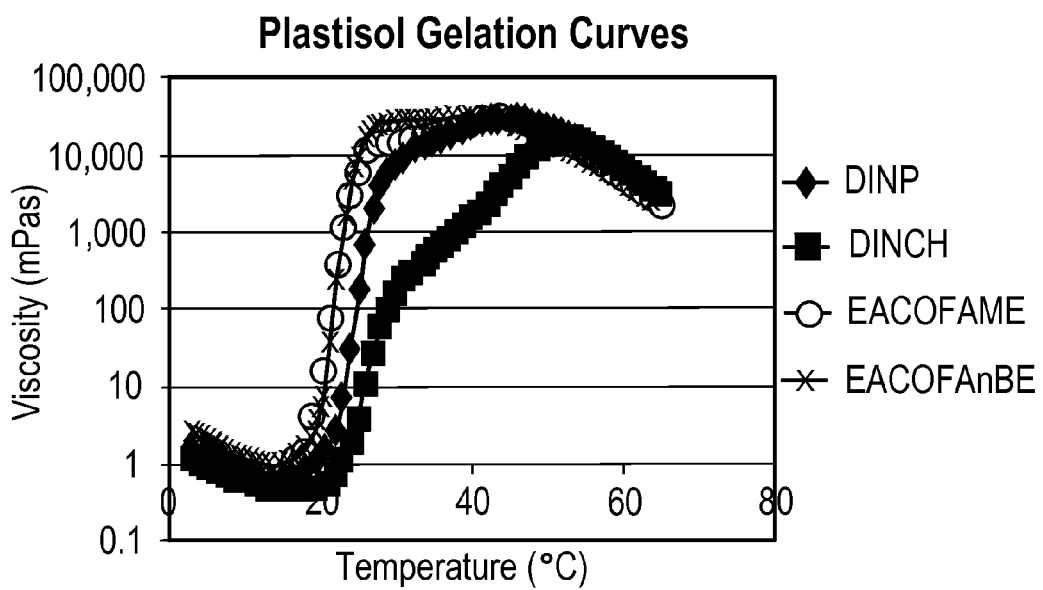
FIG. 10 illustrates the gelation behavior of plastisols prepared with EACOFAME and EACOFAnBE plasticizers, compared to commercial DINP and DINCH plasticizers.
Figure 11:
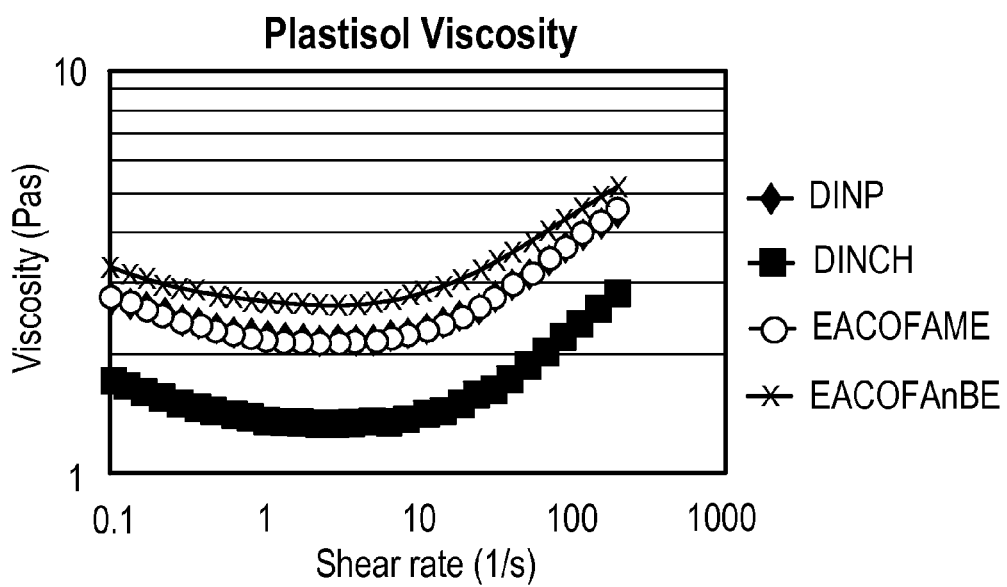
FIG. 11 illustrates viscosity profiles for plastisols prepared with EACOFAME and EACOFAnBE plasticizers, compared to commercial DINP and DINCH plasticizers.
Figure 12:
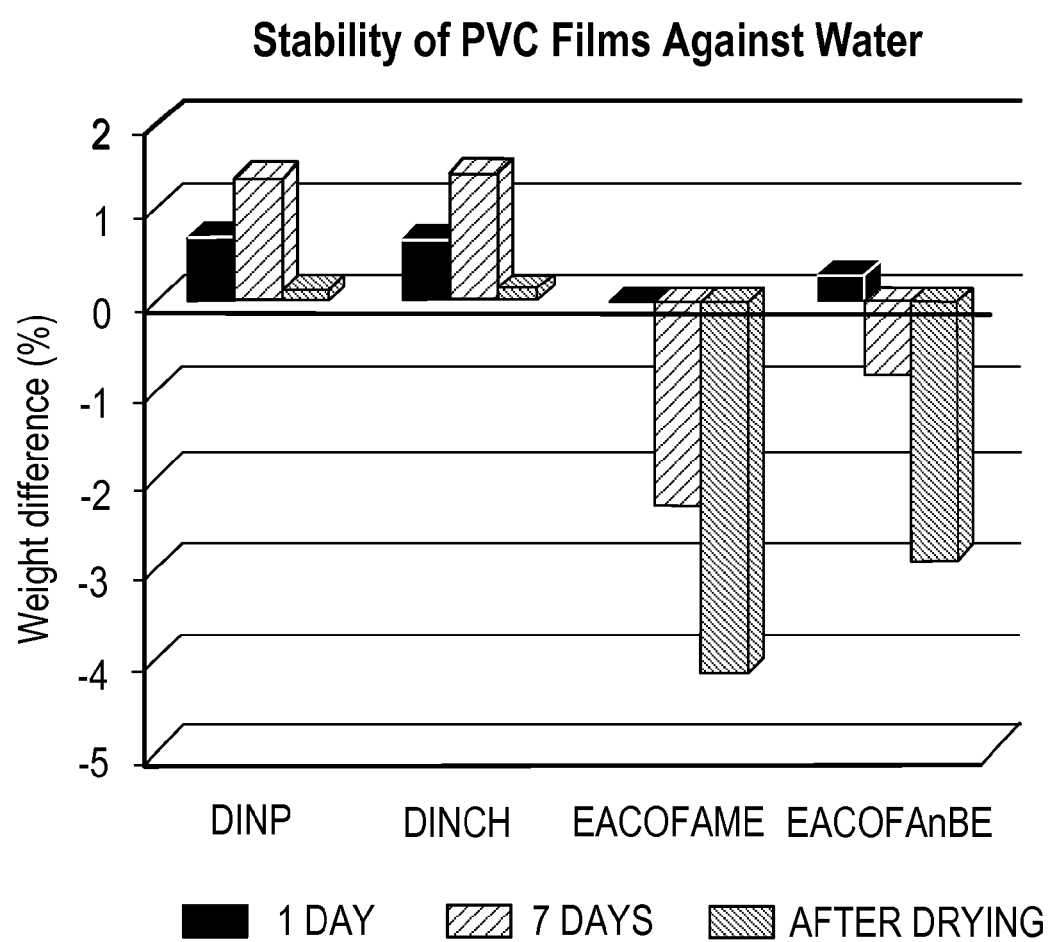
FIG. 12 illustrates the stability in water for plastisols prepared with EACOFAME and EACOFAnBE plasticizers, compared to commercial DINP and DINCH plasticizers.

To determine the stability of the plasticizers in water, each plastisol was placed in water for seven days and the weight difference was measured at days 1, 7, and after drying the sample. These weight differences were graphed and are shown in FIG. 7. EAFAME shows a greater migration out of PVC than EAFAnBE and the commercial plasticizers. The n-butyl ester functionality leads to better water stability useful in applications with high water contact.

Plasticizer exudation for each plastisol strip was measured according to the ASTM D3291 test method. In this method, the plastisol strips are bent 180° and held in that position for several days. The amount of spew or beads of liquid seen after removing the pieces and bending them 360° is noted for each specimens after days 1, 7, and 14. Even after 14 days, none of the plastisol strips exhibited any plasticizer exudation, indicating that the plasticizers exhibited good compatibility with PVC.

B. EACOFAME and EACOFAnBE

PVC plastisols containing EACOFAME and EACOFAnBE were prepared using the procedure described above for EAFAME and EAFAnBe. The volatility of the plasticizer upon heating to 200° C., the Shore A hardness of a plastisol film, the plastisol gelation behavior, the plastisol viscosity, and water stability were evaluated using the procedures described above for EAFAME and EACOFAnBe plastisols, and compared to plastisols prepared using DINP and DINCH. The results are shown in FIGS. 8-12.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising epoxy estolide fatty acid alkyl esters derived from triacylglycerol oil having an unsaturation of greater than 80 IV, wherein the estolide is derived from an epoxy group.

2. The composition according to claim 1 wherein the oil is selected from the group consisting of soybean oil, castor oil, canola oil, rapeseed oil, sunflower oil, corn oil, safflower oil, camelina oil, linseed oil, and combinations thereof.

3. The composition according to claim 1 wherein the oil comprises soybean oil.

4. The composition according to claim 1 wherein the oil comprises castor oil.

5. The composition according to claim 1 wherein the fatty acid alkyl esters comprise C1-C6 alkyl esters.

6. The composition according to claim 5 wherein the fatty acid alkyl esters comprise a methyl ester.

7. The composition according to claim 5 wherein the fatty acid alkyl esters comprise an n-butyl ester.

8. The composition according to claim 1 wherein the epoxy estolide esters are derived from carboxylic acids having 1 to 4 carbon atoms.

9. The composition according to claim 8 wherein the epoxy estolide esters are acetate esters.

10. A plasticized composition comprising a polymer matrix and the composition of claim 1.

11. The composition according to claim 10 wherein the polymer matrix comprises polyvinyl chloride.

12. The composition according to claim 10 wherein the polymer matrix comprises a biopolymer.

13. The composition according to claim 12 wherein the biopolymer comprises a polylactide polymer.

14. The composition according to claim 12 wherein the biopolymer comprises a cellulosic polymer.

15. The composition according to claim 1 wherein the fatty acid alkyl esters comprise C1-C12 alkyl esters.

* * * * *